United States Patent [19]
Dente et al.

[11] Patent Number: 5,847,208
[45] Date of Patent: Dec. 8, 1998

[54] METHOD FOR INCREASING THE YIELD AND THE PRODUCTION POTENTIAL OF UREA REACTORS

[75] Inventors: Mario Dente; Sergio Bozzano, both of Milan, Italy

[73] Assignee: Urea Casale, S.A., Switzerland

[21] Appl. No.: 900,151

[22] Filed: Jul. 28, 1997

Related U.S. Application Data

[63] Continuation of Ser. No. 478,692, Jun. 7, 1995, abandoned, which is a continuation of Ser. No. 205,096, Mar. 3, 1994, abandoned, which is a continuation of Ser. No. 821,428, Jan. 15, 1992, Pat. No. 5,304,353.

[30] Foreign Application Priority Data

Jan. 15, 1991 [CH] Switzerland ............... 00103/91

[51] Int. Cl.$^6$ ............................... C07C 273/04
[52] U.S. Cl. ................. 564/67; 564/68; 564/69; 564/70; 564/71; 564/72; 422/193; 422/311; 423/238; 423/359
[58] Field of Search ............... 564/67, 68, 69, 564/70, 71, 72, 73; 423/238, 359; 422/193, 311

[56] References Cited

U.S. PATENT DOCUMENTS

| | | | |
|---|---|---|---|
| 2,973,189 | 2/1961 | Chu | 202/158 |
| 3,049,563 | 8/1962 | Bochinski et al. | 546/70 |
| 3,070,360 | 12/1962 | Rafferty et al. | 202/158 |
| 3,143,482 | 8/1964 | McLeod et al. | 202/158 |
| 3,222,040 | 12/1965 | Eckert | 261/94 |
| 3,568,462 | 3/1971 | Hoffman et al. | 261/112.2 |
| 3,717,553 | 2/1973 | Otsuki et al. | 261/114.3 |
| 4,098,579 | 7/1978 | Starzycki et al. | 564/67 |
| 4,291,006 | 9/1981 | Pagani et al. | 564/69 |
| 4,315,803 | 2/1982 | Strang, Sr. | 261/114.1 |
| 4,356,132 | 10/1982 | Belyakov et al. | 261/114.3 |
| 4,552,979 | 11/1985 | Stokes | 564/69 |
| 4,604,247 | 8/1986 | Chen et al. | 261/112.2 |
| 4,929,399 | 5/1990 | Lockett et al. | 261/112.2 |

FOREIGN PATENT DOCUMENTS

| | | |
|---|---|---|
| 0011976 | 6/1980 | European Pat. Off. . |
| 344716 | 4/1960 | Switzerland . |

*Primary Examiner*—Shailendra Kumar
*Attorney, Agent, or Firm*—Ostrolenk, Faber, Gerb & Soffen, LLP

[57] ABSTRACT

Urea is formed by the synthesis of ammonia with carbon dioxide at high pressure and temperature in an internal space of reactors through which flow a liquid phase cocurrently with a gas phase. The reactors are divided into compartments to avoid excessive mixing of the entire liquid phase and to allow the intermittent redistribution of the gas in bubbles of a suitable size for increasing the transfer of heat and mass between the two phases. At each passage from one compartment to the next, the liquid phase and the gas phase are made to flow on separate routes and are distributed in each compartment with a continuous, permanent, and even flow.

21 Claims, 3 Drawing Sheets

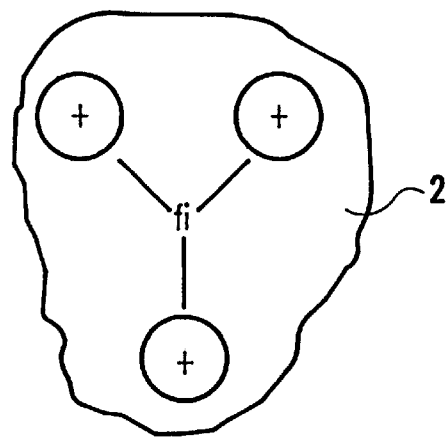
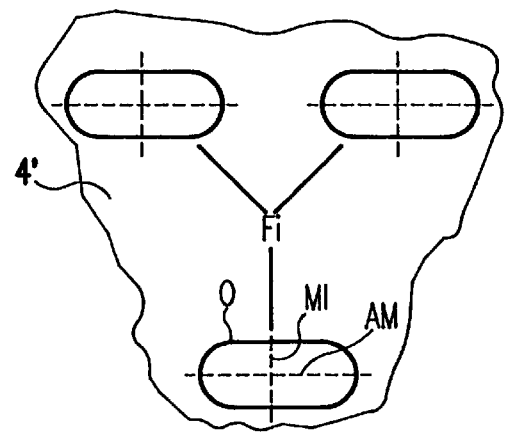
FIG.5  FIG.5A
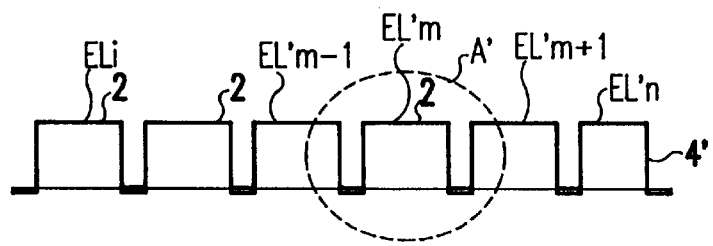
FIG.4
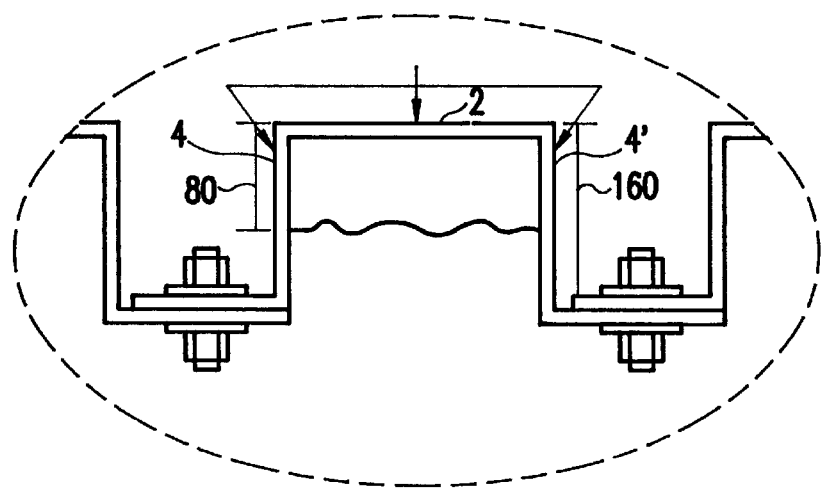
FIG.4A

METHOD FOR INCREASING THE YIELD AND THE PRODUCTION POTENTIAL OF UREA REACTORS

This is a continuation of application Ser. No. 08/478,692 filed on Jun. 7, 1995, now abandoned, which is a continuation of application Ser. No. 08/205,096 filed on Mar. 3, 1994, now abandoned, which is a continuation of application Ser. No. 07/821,428 filed on Jan. 15, 1992, now U.S. Pat. No. 5,304,353.

BACKGROUND OF THE INVENTION

1. Field of the Invention

This invention concerns increasing the yield while at the same time increasing the production potential of reactors for producing urea, formed by synthesis between ammonia and carbon dioxide at high pressure and temperature. The reactors include an internal space for cocurrent fluid flow by a liquid phase and a gas phase, the internal space being divided into compartments to avoid excessive mixing of the liquid phase and to allow for intermittent redistribution of gas in bubbles of a size suitable for increasing heat and matter exchange between the two phases.

The invention also concerns a device including several perforated flat baffles or plates distributed transversely in a cylindric reactor shell for creating compartments therein, through which flow gas and liquid containing urea.

2. Description of the Related Art

In modern reactors for the synthesis of urea, two phase (a gas phase and a liquid phase) flow cocurrently inside the cylindrical shell of the reactor (which is under pressure). The shell is divided into compartments by several perforated plates. The purpose of this configuration is to avoid excessive mixing of the entire liquid phase contained in the reactor, which would tend to turn it into a complete mixing reactor, thus reducing the urea yield. The amount of mixing is reduced by dividing the reactor into several stages by means of several plates. The behavior of the liquid phase approaches that of the behavior of a piston flow reactor, which is notoriously the most favorable for keeping the urea yield relatively high.

By dividing the reactor into several stages by means of perforated plates, it is also possible to redistribute the gas which flows upwards along the column intermittently in smaller bubbles more suitable for increasing heat and mass transfer between the two phases. In effect, the rising showers of bubbles are subjected to coalescence phenomena which progressively increase the size of the bubbles, thus reducing the exchange surface between phases. This negative phenomena is partly compensated for by the redistribution brought about by the perforated flat plates.

However, the cocurrent flow of gas and liquid over each perforated plate produces some adverse effects on both the heat and mass transfer and consequently the urea yield. The latter is due to a diminution of the flow of reagents into the liquid phase, as well as to the reduction in temperature because of the smaller exothermic reaction and also to the reduction in the liquid hold-up in the reactor. In effect, gas and liquid cannot go through the perforations in the flat baffles simultaneously, but are forced to do so alternately by means of forming showers of gas bubbles, separated by liquid pistons in continuous phase. Such an arrangement, as compared with a uniform distribution of the bubbles with the same amount of gas brings about a higher concentration of bubbles inside the showers alternating with the liquid pistons. The result is a significant increase in coalescence of the bubbles between one plate and the next (increasing their average size), a reduction of the gas/liquid transfer surface, and a worsening of the gas phase/liquid phase transfer since less gas is transferred to the liquid phase. The volume available for this phase is also reduced (and the temperature it has reached is also lowered). Moreover, between the plates and the cylinder there is in general a circular slit through which part of the gas may go with less transfer efficiency. All this causes a reduction of the urea yield, compared with the yield obtainable with a uniform distribution.

Also, the possibility of increasing the production potential in reactors in existing plants is limited. Generally, the reactor, due to its potential liquid phase capacity, is very large compared to the nominal urea production required of it, and this fact would lend itself, in principle, to possible increases in production with an almost constant urea yield. However, urea yield drastically worsens as the gas and liquid capacity increases, because of the poor distribution of gas, the size of the bubbles due to parasitical coalescence, the mass and heat transfer between phases, the effective volume left to the liquid phase (in which the reaction forming the urea takes place). Accordingly, urea production does not increase proportionately to the increase in total liquid and gas capacity.

SUMMARY OF THE INVENTION

The main purpose of this invention is to provide a method to eliminate the above-mentioned drawbacks and to increase the synthesis reaction yield and the potential of urea reactors.

Another purpose of the invention is to provide particularly simple and efficient devices to put into effect the method. In every transfer from one compartment into the other the gas and liquid phases are made to flow in mutually separate and distributed ways, each with a continuous, permanent and even flow.

In a preferred embodiment, a device is provided including perforations in plates having dimensional and/or shape gradients which create area fractions which permit the flow of liquid in the substantial absence of gas bubbles. The bubbles sliding and being evenly distributed and concentrated in an area which would be hard to reach by the liquid.

Therefore, according to an aspect of this invention, the reactor's perforated plates are made in such a way as to allow the more even distribution, with a permanent flow, of the gas bubbles avoiding their coalescing between plates and the adverse effects of the two-phase movement discussed above with showers of bubbles alternating with a continuous liquid flow. The result is an increase in urea yield and of the reactor's production potential.

In a particularly simple and efficient and therefore preferred embodiment, the plates are differently perforated and shaped in such a way as to allow the continuous and permanent flow of both the gas and the liquid, both flowing along routes which are mutually separate and distributed through each plate. The size of the perforations is different for the area of the plate for the flow of liquid and the flow of gas. The size of the perforations in the areas intended for the flow of liquid being such as to impede the passage through them of gas bubbles together with the liquid, but rather to favor sliding of the bubbles toward zones intended for the gas flow. The area for the flow of the two phases are distributed in such a way as to ensure the even distribution of the gas bubbles through said shaped perforated plates.

BRIEF DESCRIPTION OF THE DRAWINGS

The various aspects and advantages of the invention will be made more clear by the description of the embodiment represented in the drawings in which:

FIG. 4 is a front view of a plate formed by rectangular elements;

FIG. 4A is an enlarged view of the portion of the plates circled and labeled A' in FIG. 4;

FIGS. 5 and 5A are enlarged views of perforated portions of upper parts of the plates.

DETAILED DESCRIPTION OF THE PREFERRED EMBODIMENTS

Figure 1:
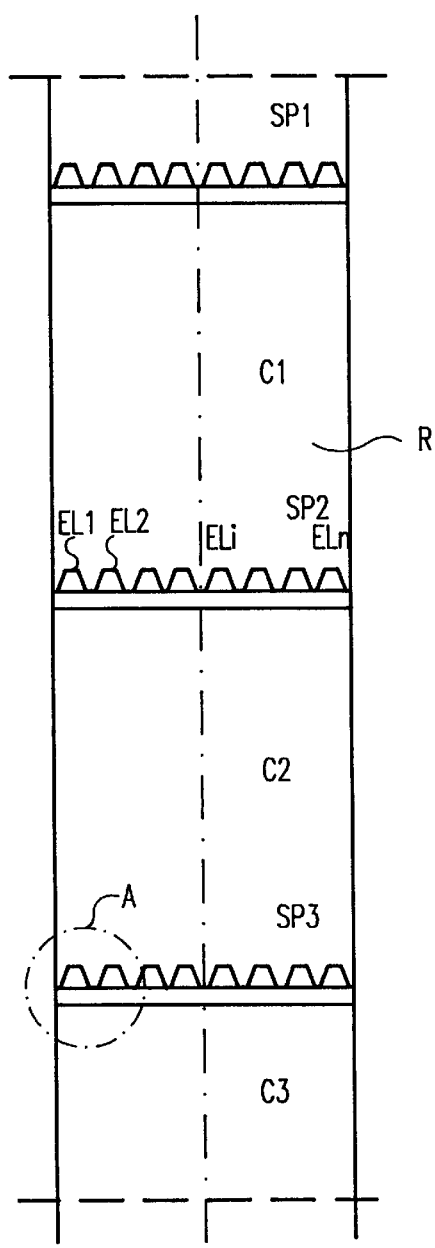
FIG. 1 shows a schematic and partial longitudinal cross-sectional view of a multi-compartment reactor in accordance with the invention.

In FIG. 1, R shows the central cylindrical shell of the urea reactor and C1, C2, C3 are three transversal compartments created by the three plates SP1, SP2 and SP3. These are formed by the lozenge-shaped elements EL1 ... ELn which in FIG. 2 are trapeze-shaped and which in FIG. 4 are preferably rectangular.

Figure 2:
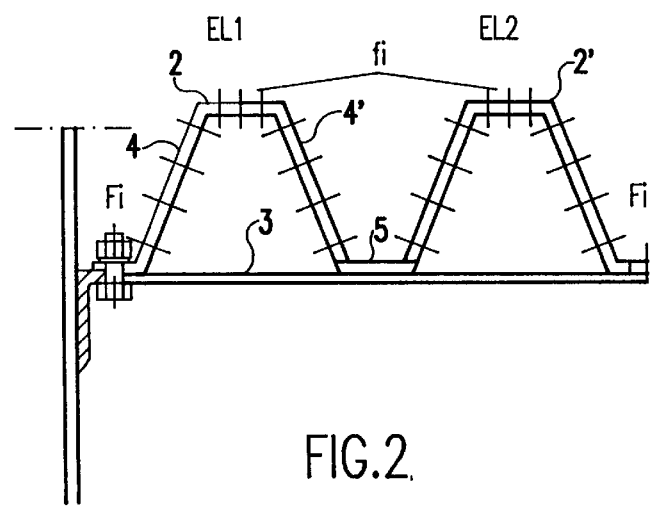
FIG. 2 is an enlarged scale view of the elements forming the plates of the reactor and circled and labeled A in FIG. 1.

FIG. 2 shows that every EL1 element is shaped like a Greek key, with a wall shaped like an upside down trapeze formed by the side or lesser base 2 at the top, by the greater base at the bottom 3, by the two slanting sides 4 and 4', and by airspace 5. According to the main aspect of the invention, in the embodiment shown in FIG. 2, on the two slanting sides 4 and 4' there are perforations Fi larger than perforations fi on wall 2. Preferably, perforations fi have a diameter which is between 1 and 3.5 mm, most preferably, about 2 to 3 mm, while the large perforations Fi have a diameter which is almost twice that of fi, i.e., 2 to 7 mm, perforations Fi being preferably 3 to 6 mm.

Figure 3:
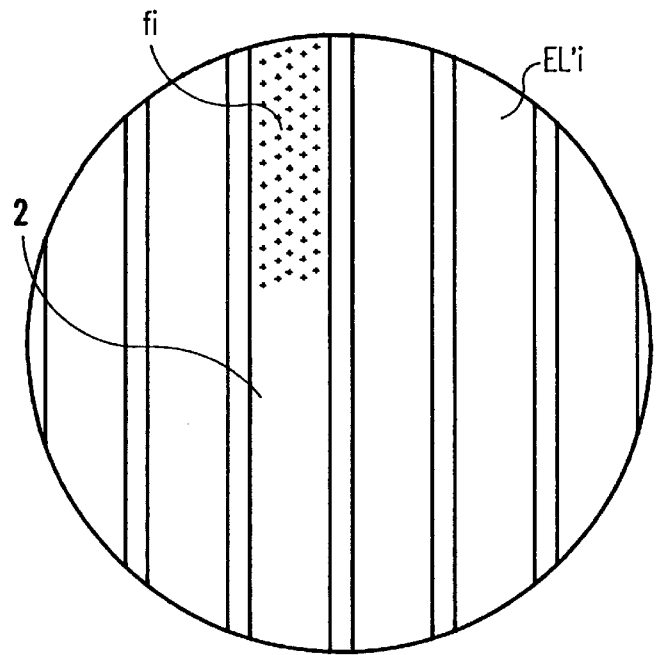
FIG. 3 is a top view of an upper part of the plates.
Figure 3A:
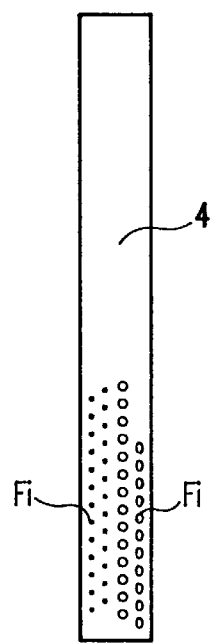
FIG. 3A shows the side of the plates.

FIG. 3 shows a top view of a wall 2 of a rectangular or trapeze-shaped element EL'i.

FIG. 4 shows the front view of a flat baffle, perforated and formed by elements from EL'1 to EL'n which are rectangular, i.e., with walls 4 and 4' parallel with the reactor's axis.

Perforations fi on wall 2 are generally circular as in FIG. 5. On the other hand, perforations Fi on walls 4 and 4' may be substantially ellipse-shaped as shown in FIG. 5A as 0. They are characterized by a greater axis AM and by a smaller axis MI.

EXAMPLE

Operations have been carried out by simulation on a reactor whose model has supplied, under nominal design conditions, for a production of about 1800 t/d, a yield of 64% on the total flow (liquid plus gas). If the yield were to be (improperly) estimated on the sole liquid phase, it would be about 65.5%. By increasing production up to about 2300 t/d, a diminution in yield was noticed. This confirms, indirectly, a) that the reactor is far too big, b) that an improvement in transport processes inside the reactor would not only increase the yield, compared to nominal conditions, but would also improve yield which would be maintained throughout notable increases of its potential.

Operations were then continued by simulating with a rigorous mathematical model conditions for a daily production of 2300 t. in the unmodified reactor. A yield (simulated) was obtained of 61.3% which, if based (improperly) on the sole liquid phase would yield 63.5%. The absence of a number of data under these conditions does not allow for immediate confirmation, but it would seem that the effective yield predicted by the model under increased production conditions is reasonably close to reality.

Simulation (through the model) of introducing into the reactor new plates in the 16 meters of the lower tangential line of the reactor was then carried out. The model modified in accordance with the invention has shown (for the potential of 2300 t/d already achieved) a yield (i.e., the molar percent of $CO_2$ converted) of 65.8% (+4.5% absolute) in respect of the total flow (equal to, improperly, 66.7% on the liquid phase, but with a drastic reduction in gas).

It has also been confirmed that such yield can be maintained for further increases in potential up to 2700 t/d (if that were made possible by the other equipment in the plant). This is a further advantage of the invention.

Consequently, in theory, under the conditions taken into consideration, an increase in yield (simulated) of 4.5% absolute could be obtained and further increases in production would be tolerable.

Some elements resulting from experiments are given below.

In the description which follows, linear dimensions for baffles and for the passage of liquids are indicative. If necessary for construction purposes, they can be varied by about 50–10%.

This also applies to the number of perforations per square meter both where the liquid phase and the gas phase passes.

On the other hand, the size of the perforations for the gas phase must be considered unchangeable while those for the liquid phase are virtually so.

Finally, it is confirmed that the number of perforations per square meter for the gas phase and the liquid phase should be read as referred to the areas for the gas phase and the liquid phase and not to the total area (gas plus liquid).

Numbering of the plates (suggested, or actually existing, for that part which has not been replaced) begins at the lower tangential line (T.L.) of the reactor (not shown on drawings).

In the same way, when the plates are being installed they should be rotated alternately (in respect of the dome directrix) by 60°–90°, insofar as fastening points allow.

It has been found that, on the whole, the following instructions should be followed when making the plates:

the thickness of the metal should not be more than 3.5–4 mm, to permit punching of the perforations;

the plates should be oriented alternately, for example, fixing them at right angles or at 60°;

perforations for the installation should be made on that portion of the sheet metal reserved for the passage of liquid;

perforations per square meter for the surface intended for the passage of gas should be understood as referring to the entire surface of the sheet metal, even that which after being folded becomes lateral (vertical);

perforations for the gas should be made in equilateral triangular links with a 24 mm pitch;

after the plate has been shaped it is essential that the baffles are closed at the ends with vertical walls welded to the terminal sections creating a seal to avoid gas escaping from the sides;

to make up for the thinness suitable supports or stiffeners can be applied to the sheet metal after perforating and shaping;

the gas should be introduced into the lower part through a horizontal tube with multiple perforations set at right angles to the baffles of the lowest plate: if this were not possible, it would become necessary to arrange two plates, with baffles at right angles between them, close to one another (300–500 mm) which would obtain the same result (since the lower plate would act as a distributor for the upper plate).

The plates should be at a distance of about 2.4 m.

Perforations for the gas could, in principle, be varied from one plate to the other, with a perforated area decreasing from bottom towards the top; however, with the plates arranged according to the invention, it is possible to maintain even perforations equal to the maximum perforations required for the lower plate. This simplifies construction and installation procedures. In the upper plates, the vapors (gas) are gradually decreasing, resulting in an increase of the level of the liquids inside the domes and a decrease of the head of gas (part of the perforations for the passage of gas will therefore be used by the liquid).

In a preferred embodiment:

perforations for the gas (in the present case) were 2000 holes/(square meter of relative area) with a diameter $\varnothing=3$ mm; arranged as an equilateral triangle (preferred arrangement), this means a distance between perforations, for example, of 24 mm (and a fraction of perforated area, on the area intended for gas, of 1.4%) (FIG. 5);

perforations for the liquid (in the present case), 600 holes/(square meter of relative area) with diameter $\varnothing=8$ mm, arranged as an equilateral triangle with a distance of 43 mm. Where oval perforations are used (FIG. 5A), their axes are 4 mm–6 mm, interspersed in the same way (with a fraction of perforated area of about 3% of the area for the liquid).

Obviously, the metallic strips bearing the perforations, after being folded and installed, should be bolted one to another, leaving an edge for the alternating overlap from one dome to the next.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

We claim:

1. A method for producing urea and simultaneously increasing production potential of the reactor, the urea being synthesized in an internal space of the reactor from ammonia and carbon dioxide at high pressure and temperature in a concurrent upward flow of a liquid phase and a gas phase, the reactor being divided into compartments for avoiding excessive mixing of the liquid phase and to intermittently redistribute the gas phase in bubbles of a size suitable for increasing heat and mass transfer between the phases, the method comprising the step of flowing the liquid phase and gas phase through mutually separate routes between compartments of the reactor, wherein the flowing step comprises:

separating the liquid phase from the gas phase;

flowing predominantly the liquid phase through a plurality of first openings in a separating means defining the compartments of the reactor, the first openings have a first predetermined size; and flowing predominantly the gas phase through a plurality of second openings in the separating means, the second openings having a second predetermined size, the first openings favoring flow therethrough of the liquid phase and the second openings favoring flow therethrough of the gas phase, whereby each of the liquid phase and the gas phase are distributed through the reactor in a substantially even, continuous and permanent flow, the liquid phase being separated from the gas phase below said separating means.

2. A method according to claim 1, wherein at least one of said separating means comprises a plurality of elements having one of a rectangular cross section or trapezoidal cross section, said elements extending upwardly from said plate and being open at the bottom, each said element comprising:

two perforated side walls defining a first area containing said first openings, and a perforated top wall defining a second area containing said second openings, said openings in the top wall being smaller in size than the openings in the side walls.

3. A method according to claim 2, wherein at least one of said separating means comprises a plurality of elements having rectangular cross-sections.

4. A method according to claim 2, wherein at least one of said separating means comprises a plurality of elements having trapezoidal cross-sections.

5. A method according to claims 3, wherein the openings in the side walls of said elements have a diameter of 2 to 8 mm.

6. A method according to claim 5, wherein the openings in the side walls of said elements have a diameter of from 3 to 6 mm.

7. A method according to claims 3, wherein the openings in the top wall of said elements have a diameter of 1 to 3.5 mm.

8. A method according to claim 7, wherein the openings in the top wall of said elements have a diameter of from 2 to 3 mm.

9. A method according to claims 3, wherein the openings in the side walls of said elements are oval-shaped.

10. A method according to claims 3, wherein the openings in the top wall of said elements are round.

11. In a method for producing urea from ammonia and carbon dioxide at high pressure and temperature, the improvement comprising the step of flowing a liquid phase and a gas phase through mutually separate routes between compartments of a reactor for producing urea, wherein the flowing step comprises:

separating the liquid phase from the gas phase;

flowing predominantly the liquid phase through a plurality of first openings in a separating means defining the compartments of the reactor, the first openings having a first predetermined size; and flowing predominantly the gas phase through a plurality of second openings in the separating means, the second openings having a second predetermined size, the first openings favoring flow therethrough of the liquid phase and the second openings favoring flow therethrough of the gas phase, whereby each of the liquid phase and the gas phase are distributed through the reactor in a substantially even, continuous and permanent flow.

12. A method according to claim 11, wherein at least one of said separating means comprises a plurality of elements having one of a rectangular cross section or trapezoidal cross section, said elements extending upwardly from said plate and being open at the bottom, each said element comprising:

two perforated side walls defining a first area containing first openings, and a perforated top wall defining a second area containing said second openings, said openings in the top wall being smaller in size than the openings in the side walls.

13. A method according to claim 12, wherein at least one of said separating means comprises a plurality of elements having rectangular cross-sections.

14. A method according to claim 12, wherein at least one of said separating means comprises a plurality of elements having trapezoidal cross-sections.

15. A method according to claims 13, wherein the openings in the side walls of said elements have a diameter of 2 to 8 mm.

16. A method according to claim 15, wherein the opening is in the side walls of said elements have a diameter of from 3 to 6 mm.

17. A method according to claims 13, wherein the openings in the top wall of said elements have a diameter of 1 to 3.5 mm.

18. A method according to claim 17, wherein the openings in the top wall of said elements have a diameter of from 2 to 3 mm.

19. A method according to claims 13, wherein the openings in the side walls of said elements are oval-shaped.

20. A method according to claims 13, wherein the openings in the top wall of said elements are round.

21. A method according to claim 11, wherein said first openings create a first area fraction which permits obtaining a liquid flow in the substantial absence of gas bubbles and said second openings create a second area fraction, above the level of liquid inlet of the first area fraction, said second area fraction having an area smaller than the area of the first area fraction which permits obtaining a concentration of gas in a zone which would be hardly reached by the liquid and a gas flow in the substantial absence of liquid from said zone.

* * * * *